(12) United States Patent
Bakos

(10) Patent No.: US 8,002,714 B2
(45) Date of Patent: Aug. 23, 2011

(54) GUIDEWIRE STRUCTURE INCLUDING A MEDICAL GUIDEWIRE AND METHOD FOR USING A MEDICAL INSTRUMENT

(75) Inventor: Gregory J. Bakos, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1404 days.

(21) Appl. No.: 11/505,608

(22) Filed: Aug. 17, 2006

(65) Prior Publication Data
US 2008/0058679 A1 Mar. 6, 2008

(51) Int. Cl.
*A61B 5/00* (2006.01)
*A61M 5/178* (2006.01)

(52) U.S. Cl. .................. 600/585; 604/164.13
(58) Field of Classification Search ............. 600/585, 600/433–435; 604/164.01, 164.13
See application file for complete search history.

(56) References Cited

U.S. PATENT DOCUMENTS

| | | | |
|---|---|---|---|
| 1,891,054 A | 12/1932 | Pitman | |
| 2,856,934 A * | 10/1958 | Petillo | 604/170.01 |
| 3,892,228 A | 7/1975 | Mitsui | |
| 4,176,662 A | 12/1979 | Frazer | |
| 4,207,872 A | 6/1980 | Meiri et al. | |
| 4,224,929 A | 9/1980 | Furihata | |
| 4,326,530 A | 4/1982 | Fleury, Jr. | |
| 4,447,227 A | 5/1984 | Kotsanis | |
| 4,686,965 A | 8/1987 | Bonnet et al. | |
| 4,947,827 A | 8/1990 | Opie et al. | |
| 5,025,778 A | 6/1991 | Silverstein et al. | |
| 5,054,501 A | 10/1991 | Chuttani et al. | |
| 5,078,716 A | 1/1992 | Doll | |
| 5,113,872 A | 5/1992 | Jahrmarkt et al. | |
| 5,154,164 A | 10/1992 | Chikama | |
| 5,217,001 A | 6/1993 | Nakao et al. | |
| 5,238,004 A * | 8/1993 | Sahatjian et al. | 600/585 |
| 5,333,620 A * | 8/1994 | Moutafis et al. | 600/585 |
| 5,337,732 A | 8/1994 | Grundfest et al. | |
| 5,345,925 A | 9/1994 | Allred, III et al. | |
| 5,360,403 A | 11/1994 | Mische | |
| 5,363,847 A | 11/1994 | Viera | |
| 5,385,152 A * | 1/1995 | Abele et al. | 600/585 |
| 5,398,670 A | 3/1995 | Stubbs et al. | |
| 5,489,256 A | 2/1996 | Adair | |
| 5,503,616 A | 4/1996 | Jones | |
| 5,505,686 A | 4/1996 | Willis et al. | |

(Continued)

FOREIGN PATENT DOCUMENTS

AU 2003271310 10/2004

(Continued)

*Primary Examiner* — Theodore J Stigell
*Assistant Examiner* — Andrew M Gilbert

(57) ABSTRACT

A first guidewire structure includes a medical guidewire having a working portion which is extendable beyond a distal end of a medical instrument. The working portion has a length, and the working portion is tapered for substantially one-hundred percent of the length. A second guidewire structure includes a medical guidewire having a working portion, wherein the working portion has a length, and wherein the working portion includes a tapered portion for over fifty percent of the length. A third guidewire structure includes a medical guidewire having a working portion. The working portion has a length, and the working portion includes a plurality of lengthwise-adjoining segment pairs for over fifty percent of the length. Each segment pair consists essentially of a non-tapered segment having a substantially constant cross section and a tapered segment lengthwise adjoining the non-tapered segment. Methods are described for using medical instruments having the guidewire structures.

19 Claims, 7 Drawing Sheets

U.S. PATENT DOCUMENTS

| | | | |
|---|---|---|---|
| 5,522,819 | A | 6/1996 | Graves et al. |
| 5,595,565 | A | 1/1997 | Trimmer |
| 5,604,531 | A | 2/1997 | Iddan et al. |
| 5,643,175 | A | 7/1997 | Adair |
| 5,645,519 | A | 7/1997 | Lee et al. |
| 5,730,704 | A | 3/1998 | Avitall |
| 5,749,889 | A | 5/1998 | Bacich et al. |
| 5,772,609 | A * | 6/1998 | Nguyen et al. ............... 600/585 |
| 5,836,947 | A | 11/1998 | Fleishmann et al. |
| 5,882,293 | A | 3/1999 | Ouchi |
| 5,891,055 | A | 4/1999 | Sauter |
| 5,895,417 | A | 4/1999 | Anderson et al. |
| 5,904,648 | A | 5/1999 | Arndt et al. |
| 5,944,654 | A | 8/1999 | Crawford |
| 5,984,860 | A | 11/1999 | Shan |
| 6,007,482 | A | 12/1999 | Madni et al. |
| 6,036,636 | A | 3/2000 | Konomura |
| 6,059,719 | A | 5/2000 | Yamamoto et al. |
| 6,106,488 | A | 8/2000 | Vogel et al. |
| 6,162,171 | A | 12/2000 | Ng et al. |
| 6,190,382 | B1 | 2/2001 | Ormsby |
| 6,203,525 | B1 | 3/2001 | Whayne et al. |
| 6,238,389 | B1 | 5/2001 | Paddock |
| 6,241,702 | B1 | 6/2001 | Lundquist |
| 6,309,346 | B1 | 10/2001 | Farhadi |
| 6,352,503 | B1 | 3/2002 | Matsui |
| 6,355,034 | B2 | 3/2002 | Cosmescu |
| 6,359,379 | B1 | 3/2002 | Lee et al. |
| 6,454,758 | B1 | 9/2002 | Fleischman et al. |
| 6,527,753 | B2 | 3/2003 | Sekine et al. |
| 6,554,942 | B2 * | 4/2003 | Solar et al. ............... 156/244.11 |
| 6,569,085 | B2 | 5/2003 | Kortenbach et al. |
| 6,666,829 | B2 * | 12/2003 | Cornish et al. ............... 600/585 |
| 6,689,130 | B2 | 2/2004 | Arai et al. |
| 6,699,180 | B2 | 3/2004 | Kobayashi |
| 6,740,030 | B2 | 5/2004 | Martone et al. |
| 7,226,410 | B2 * | 6/2007 | Long ............... 600/114 |
| 7,288,074 | B2 * | 10/2007 | Swain et al. ............... 600/585 |
| 7,670,526 | B2 * | 3/2010 | Solar et al. ............... 264/260 |
| 2002/0010426 | A1 | 1/2002 | Vandenbroek et al. |
| 2002/0107530 | A1 | 8/2002 | Sauer et al. |
| 2002/0161393 | A1 | 10/2002 | Demond et al. |
| 2002/0183591 | A1 | 12/2002 | Matsuura et al. |
| 2003/0036679 | A1 | 2/2003 | Kortenbach et al. |
| 2003/0171651 | A1 | 9/2003 | Page et al. |
| 2003/0176880 | A1 | 9/2003 | Long et al. |
| 2004/0111019 | A1 * | 6/2004 | Long ............... 600/407 |
| 2004/0111020 | A1 | 6/2004 | Long et al. |
| 2004/0199087 | A1 | 10/2004 | Swain et al. |
| 2004/0199088 | A1 * | 10/2004 | Bakos et al. ............... 600/585 |
| 2004/0230095 | A1 | 11/2004 | Stefanchik et al. |
| 2004/0230096 | A1 | 11/2004 | Stefanchik et al. |
| 2005/0027214 | A1 * | 2/2005 | Murayama et al. ............ 600/585 |
| 2005/0101836 | A1 * | 5/2005 | Onuki et al. ............... 600/104 |
| 2005/0256429 | A1 | 11/2005 | Long et al. |
| 2005/0256505 | A1 | 11/2005 | Long et al. |

FOREIGN PATENT DOCUMENTS

| | | |
|---|---|---|
| EP | 0667115 A1 | 1/1995 |
| EP | 0827712 | 3/1998 |
| EP | 1284120 A1 | 2/2003 |
| EP | 1607035 | 12/2005 |
| FR | 2481915 | 11/1981 |
| JP | 2001046508 | 2/2001 |
| WO | WO 91/14391 | 10/1991 |
| WO | WO 94/05200 | 3/1994 |
| WO | WO 97/29680 | 8/1997 |
| WO | WO 97/41767 | 11/1997 |
| WO | WO 98/11816 | 3/1998 |
| WO | WO 99/19608 A1 | 5/1998 |
| WO | WO 99/27840 | 6/1999 |
| WO | WO 99/30610 | 6/1999 |
| WO | WO 99/32028 | 7/1999 |
| WO | WO 99/34726 | 7/1999 |
| WO | WO 99/53827 | 10/1999 |
| WO | WO 00/48506 A1 | 2/2000 |
| WO | WO 00/22975 | 4/2000 |
| WO | WO 00/44275 | 8/2000 |
| WO | WO 01/49165 A1 | 1/2001 |
| WO | WO 01/08548 | 2/2001 |
| WO | WO 01/67967 | 9/2001 |
| WO | 2005/113051 | 12/2005 |

* cited by examiner

US 8,002,714 B2

GUIDEWIRE STRUCTURE INCLUDING A MEDICAL GUIDEWIRE AND METHOD FOR USING A MEDICAL INSTRUMENT

FIELD OF THE INVENTION

The present invention is related generally to guidewire structures, and more particularly to a guidewire structure having a medical guidewire.

BACKGROUND OF THE INVENTION

A physician typically accesses and visualizes tissue within a patient's gastrointestinal (GI) tract with an endoscope (such as a gastroscope or a colonoscope) having a long, flexible insertion tube. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel in the insertion tube, typically about 2.5-3.5 millimeters in diameter, extending from a port in the handpiece to the distal portion of the insertion tube. A physician may insert medical devices into the working channel to help diagnose or treat tissue within the patient.

Guidewires have been used to aid the introduction of catheters (such as insertion tubes of endoscopes) and other instruments into many sites in the human body. Many medical applications and specific designs of guidewires have been for cardiovascular use. There are, however, specific challenges relating to the use of guidewires in the GI tract, as opposed to the vascular system. Thus, the bowel is more tortuous, softer and generally of larger diameter. Furthermore, in the case of the small intestine and the colon, these are longer than most arteries or veins.

Still, scientists and engineers continue to seek improved guidewire structures having a medical guidewire.

SUMMARY

A first embodiment of a guidewire structure of the invention includes a medical guidewire having a working portion which is extendable beyond a distal end of a medical instrument. The working portion has a length, and the working portion is tapered for substantially one-hundred percent of the length.

A second embodiment of a guidewire structure of the invention includes a medical guidewire having a working portion which is extendable beyond a distal end of a medical instrument. The working portion has a length, and the working portion includes a tapered portion for over fifty percent of the length.

A third embodiment of a guidewire structure of the invention includes a medical guidewire having a working portion which is extendable beyond a distal end of a medical instrument. The working portion has a length, and the working portion includes a plurality of lengthwise-adjoining segment pairs for over fifty percent of the length. Each segment pair consists essentially of a non-tapered segment having a substantially constant cross section and a tapered segment lengthwise adjoining the non-tapered segment.

A first method for using a medical instrument includes steps a) through d). The medical instrument includes a catheter having a distal end and includes a guidewire structure. The guidewire structure includes a medical guidewire operatively connected to the catheter. The medical guidewire includes a working portion which is extendable beyond the distal end of the catheter, wherein the working portion has a length, and wherein the working portion is tapered for substantially one-hundred percent of the length of the working portion. The medical guidewire includes a first guidewire leg having a free end located outside the medical instrument and outside a patient and leading to a smallest-diameter first end of the working portion and includes a second guidewire leg having a free end located outside the medical instrument and outside the patient and leading to a largest-diameter second end of the working portion. Step a) includes inserting the distal end of the catheter an initial distance into a body lumen of the patient. Step b) includes pushing the first guidewire leg to extend at least some of a smaller-diameter tapered region of the working portion beyond the distal end of the catheter. Step c) includes pushing the second guidewire leg to extend at least some of a larger-diameter tapered region of the working portion beyond the distal end of the catheter and to temporarily anchor the larger-diameter tapered region of the working portion against a wall of the body lumen. Step d) includes immobilizing the second guidewire leg with respect to the catheter and pushing the catheter a further distance into the body lumen while pulling on the first guidewire leg to retract at least some of the larger-diameter tapered region of the working portion.

A second method for using a medical instrument includes steps a) through d). The medical instrument includes a catheter having a distal end and includes a guidewire structure. The guidewire structure includes a medical guidewire operatively connected to the catheter. The medical guidewire includes a working portion which is extendable beyond the distal end of the catheter, wherein the working portion has a length, and wherein the working portion consists essentially of a tapered portion for over fifty percent of the length of the working portion and a non-tapered portion having a substantially constant diameter and extending for over twenty-five percent of the length of the working portion. The medical guidewire includes a first guidewire leg having a free end located outside the medical instrument and outside a patient and leading to a smallest-diameter first end of the working portion and includes a second guidewire leg having a free end located outside the medical instrument and outside the patient and leading to a largest-diameter second end of the working portion. Step a) includes inserting the distal end of the catheter an initial distance into a body lumen of the patient. Step b) includes pushing the first guidewire leg to extend at least some of a smaller-diameter region of the working portion beyond the distal end of the catheter. Step c) includes pushing the second guidewire leg to extend at least some of a larger-diameter tapered region of the working portion beyond the distal end of the catheter and to temporarily anchor the larger-diameter tapered region of the working portion against a wall of the body lumen. Step d) includes immobilizing the second guidewire leg with respect to the catheter and pushing the catheter a further distance into the body lumen while pulling on the first guidewire leg to retract at least some of the larger-diameter tapered region of the working portion.

A third method for using a medical instrument includes steps a) through d). The medical instrument includes a catheter having a distal end and includes a guidewire structure. The guidewire structure includes a medical guidewire operatively connected to the catheter. The medical guidewire includes a working portion which is extendable beyond the distal end of the catheter, wherein the working portion has a length, and wherein the working portion consists essentially of a plurality of segment pairs for over fifty percent of the length of the working portion with each segment pair consisting essentially of a non-tapered segment having a substantially constant diameter and a tapered segment. The plurality of segment pairs lengthwise adjoins a joining segment, which lengthwise adjoins a diverging segment, which lengthwise adjoins a substantially constant cross section segment. The medical guidewire includes a first guidewire leg having a free end located outside the Medical instrument and outside a patient and leading to a first end of the working portion which is an end of the substantially constant cross section segment and includes a second guidewire leg having a free end located outside the medical instrument and outside the patient and leading to a second end of the working portion which is a largest-diameter end of the plurality of segment pairs. Step a) includes inserting the distal end of the catheter an initial distance into a body lumen of the patient. Step b) includes pushing the first guidewire leg to extend at least some of the substantially constant cross section segment beyond the distal end of the catheter. Step c) includes pushing the second guidewire leg to extend at least some of the plurality of segment pairs beyond the distal end of the catheter and to temporarily anchor the extended segment pairs against a wall of the body lumen. Step d) includes immobilizing the second guidewire leg with respect to the catheter and pushing the catheter a further distance, into the body lumen while pulling on the first guidewire leg to retract at least some of the extended segment pairs.

Several benefits and advantages are obtained from one or more of the embodiments and methods of the invention. In one application, having a loop-track or non-loop-track medical guidewire with a tapered portion for over fifty percent, or for substantially one-hundred percent, of the length of the working portion of the medical guidewire will allow a smaller-cross-sectioned leading portion of the guidewire to be extended into a body lumen of a patient which should result in less insertion force and will allow a larger-cross-sectioned trailing portion extending into the body lumen to handle the mass of an endoscope insertion tube which is to be advanced along the extended larger-cross-sectioned trailing portion of the guidewire. The same reasoning applies to a loop-track or non-loop-track medical guidewire with a plurality of lengthwise spaced apart tapered segments having an intervening non-tapered segment of substantially constant cross section.

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, examples, etc. can be combined with any one or more of the other following-described embodiments, examples, etc.

Figure 1:
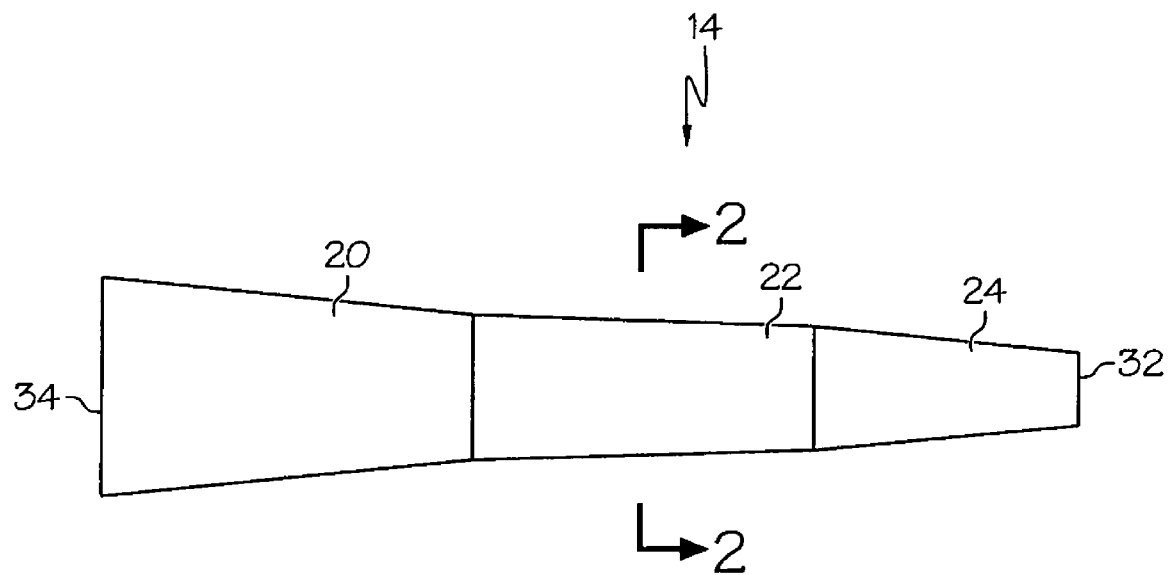
FIG. 1 is a side elevational, shortened view of a working portion of a first embodiment of a guidewire structure of the invention.
Figure 2:
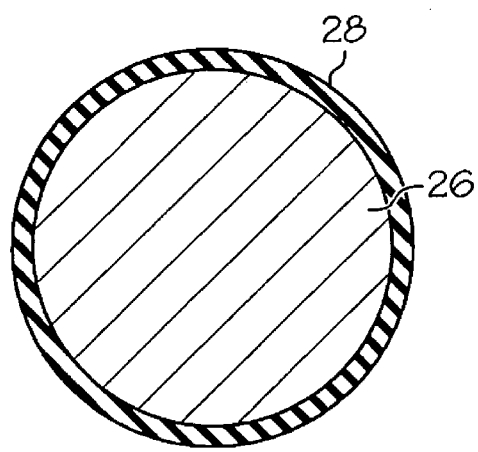
FIG. 2 is a cross-sectional view of the working portion of FIG. 1 taken along lines 2-2 of FIG. 1.
Figure 3:
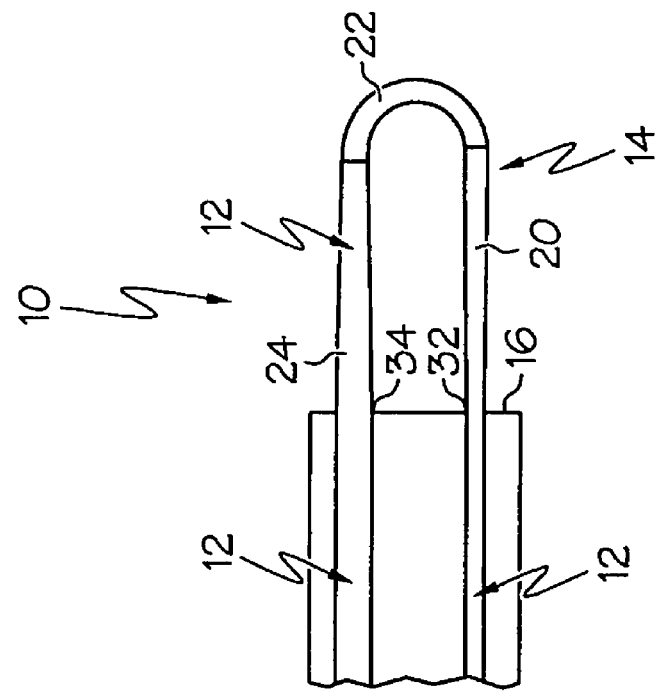
FIG. 3 is a schematic side-elevational cutaway view of a first guidewire structure having the working portion shown in FIG. 1 and employed as a loop-track guidewire in a first embodiment of a medical instrument having a catheter, wherein the entire working portion is shown extending beyond the distal end of the catheter.
Figure 3:
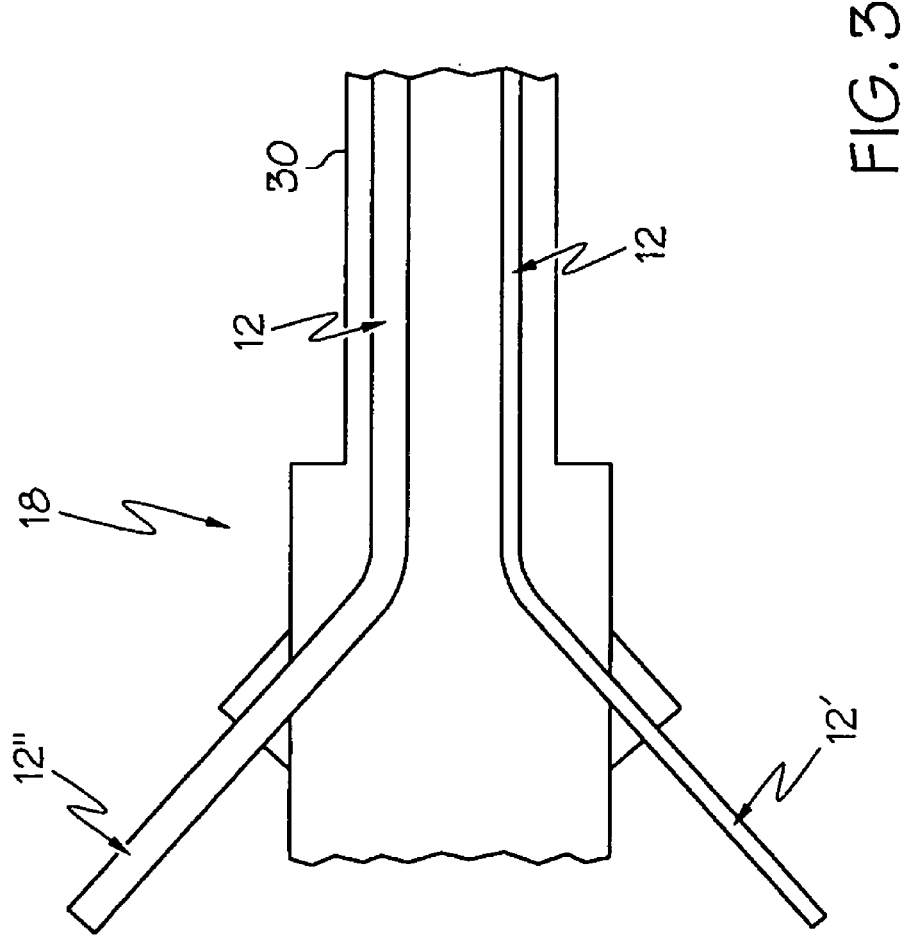

A first embodiment of a guidewire structure 10 of the invention is shown in FIGS. 1-3 and includes a medical guidewire 12. The medical guidewire 12 includes a working portion 14 which is extendable beyond a distal end 16 of a medical instrument 18. The working portion 14 has a length, and the working portion 14 is tapered for substantially one-hundred percent of the length of the working portion 14.

It is noted that the working portion 14 is a maximum portion of the medical guidewire 12 which can be extended beyond the distal end 16 of the medical instrument 18. Some applications of the guidewire structure 10 may require the entire working portion 14 to be extended beyond the distal end 16 while other applications may require less than the entire working portion 14 to be extended beyond the distal end 16. It is also noted that in some applications, the medical guidewire 12 is manually pushed (as intended by FIG. 3) to extend at least some of the working portion 14 beyond the distal end 16, that in other applications a hand crank (not shown) is used to extend at least some of the working portion 14, and that in still other applications a motor (not shown) is used to extend at least some of the working portion 14. It is further noted that, in many examples, medical guidewires are resiliently flexible.

In one enablement of the embodiment of FIGS. 1-3, the working portion 14 includes lengthwise adjoining first and second segments 20 and 22, wherein the first segment 20 has a substantially constant first taper, wherein the second segment 22 has a substantially constant second taper, and wherein the first taper is greater than the second taper. In one variation, the working portion 14 includes a third segment 24 lengthwise adjoining the second segment 22 and having a substantially constant third taper, wherein the second taper is greater than the third taper. In one example, the first segment 20 is substantially 2 meters long and tapers from a 0.040-inch cross-sectional diameter to a 0.020-inch cross-sectional diameter, the second segment 22 is substantially 1 meter long and tapers from a 0.020-inch cross-sectional diameter to a 0.018-inch cross-sectional diameter, and the third segment 24 is substantially 2 meters long and tapers from a 0.018-inch cross-sectional diameter to a 0.016-inch cross-sectional diameter.

In one implementation of the embodiment of FIGS. 1-3, the first segment 20 has a first color and the second segment 22 has a different second color. In one variation, the third segment 24 has a different third color. The different colors give a visual indication of which segment or segments are being extended beyond the distal end of the medical instrument. In the same or a different implementation, the working portion 14 includes a core wire 26 and includes a lubricious sleeve 28 surrounding, and attached to, the core wire 26. The lubricious sleeve 28 creates a low friction surface for easy passage through a body lumen of a (human or non-human) patient. Examples of materials for the lubricious sleeve 28 include, without limitation, Polytetrafluoroethylene (PTFE), such as Striped Teflon® PTFE available from Zeus, Inc (Orangeburg, S.C.). In one method, the lubricious sleeve 28 is applied over the working portion 14 through a heat-shrink process well known in the art. In one variation, the core wire 26 consists essentially of a monolithic length of a superelastic alloy such as nitinol available from Nitinol Devices & Components (Fremont, Calif.).

In a first deployment of the embodiment of FIGS. 1-3, the working portion 14 is extendable as a loop track (as shown in FIG. 3) beyond the distal end 16 of the medical instrument 18. Here, the length of the working portion 14 is a loop-track length of the working portion 14. In one variation, the medical instrument 18 has a catheter 30, and the distal end 16 is the distal end of the catheter 30. In one construction, the loop-track length of the working portion 14 is at least six feet, and the working portion 14 has a substantially circular cross-section having a maximum diameter which is always less than 0.050-inch and a minimum diameter which is always at least 0.010-inch.

In a first arrangement of the embodiment of FIGS. 1-3, the working portion 14 extends as a loop track, the medical guidewire 12 includes a first leg 12' monolithically attached to and extending from a first end 32 of the working portion 14 (which is a smallest-diameter end of the working portion 14) proximally through a first passageway of the catheter 30 and outside the medical instrument 18, and the medical guidewire 12 includes a second leg 12" monolithically attached to and extending from a second end 34 of the working portion 14 (which is a largest-diameter end of the working portion 14) proximally through a second passageway of the catheter 30 and outside the medical instrument 18. In a second arrangement, not shown, the first and second legs 12' and 12" extend through a single passageway such as a working channel of the catheter. In a third arrangement, not shown, the loop track extends beyond the distal end of the catheter from outside the exterior surface of the catheter with the first and/or second legs engaged by guide ways on the exterior surface of the catheter. Other arrangements are left to the artisan. Examples of catheters include, without limitation, cardio-vascular catheters, pulmonary catheters, and insertion tubes of endoscopes such as insertion tubes of gastroscopes and colonoscopes. In one enablement of the embodiment of FIGS. 1-3, the working portion 14 is adapted for patient intraluminal contact. Examples of body lumens of a patient include, without limitation, the upper GI (gastrointestinal) tract, the lower GI tract, and blood vessel passageways. Other examples of medical instruments 18, catheters 30, and/or body lumens are left to the artisan.

A first method for using a medical instrument 18 includes steps a) through d). The medical instrument 18 includes a catheter 30 having a distal end and includes a guidewire structure 10. The guidewire structure 10 includes a medical guidewire 12 operatively connected to the catheter 30. The medical guidewire 12 includes a working portion 14 which is extendable beyond the distal end of the catheter 30, wherein the working portion 14 has a length, and wherein the working portion 14 is tapered for substantially one-hundred percent of the length of the working portion 14. The medical guidewire 12 includes a first guidewire leg 12' having a free end disposed outside the medical instrument 18 and outside a patient and leading to a smallest-diameter first end 32 of the working portion 14 and includes a second guidewire leg 12" having a free end disposed outside the medical instrument 18 and outside the patient and leading to a largest-diameter second end 34 of the working portion 14. Step a) includes inserting the distal end of the catheter 30 an initial distance into a body lumen of the patient. Step b) includes pushing the first guidewire leg 12' to extend at least some of a smaller-diameter tapered region of the working portion 14 beyond the distal end of the catheter 30. Step c) includes pushing the second guidewire leg 12" to extend at least some of a larger-diameter tapered region of the working portion 14 beyond the distal end of the catheter 30 and to temporarily anchor the larger-diameter tapered region of the working portion 14 against a wall of the body lumen. Step d) includes immobilizing the second guidewire leg 12" with respect to the catheter 30 and pushing the catheter 30 a further distance into the body lumen while pulling on the first guidewire leg 12' to retract at least some of the larger-diameter tapered region of the working portion 14. In one extension of the method, steps b), c) and d) are repeated.

Figure 4:
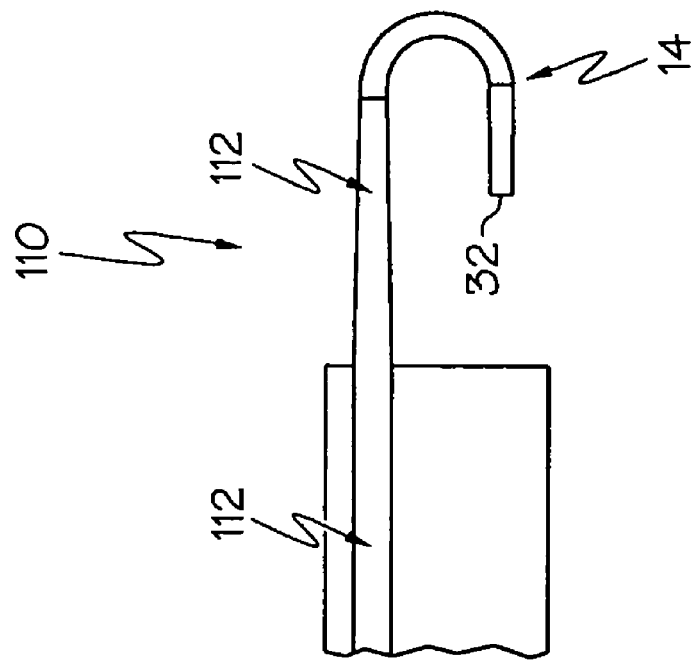
FIG. 4 is a schematic side-elevational cutaway view of a second guidewire structure having the working portion shown in FIG. 1 and employed as a non-loop-track guidewire in a second embodiment of a medical instrument having a catheter, wherein the entire working portion is shown extending beyond the distal end of the catheter.
Figure 4:
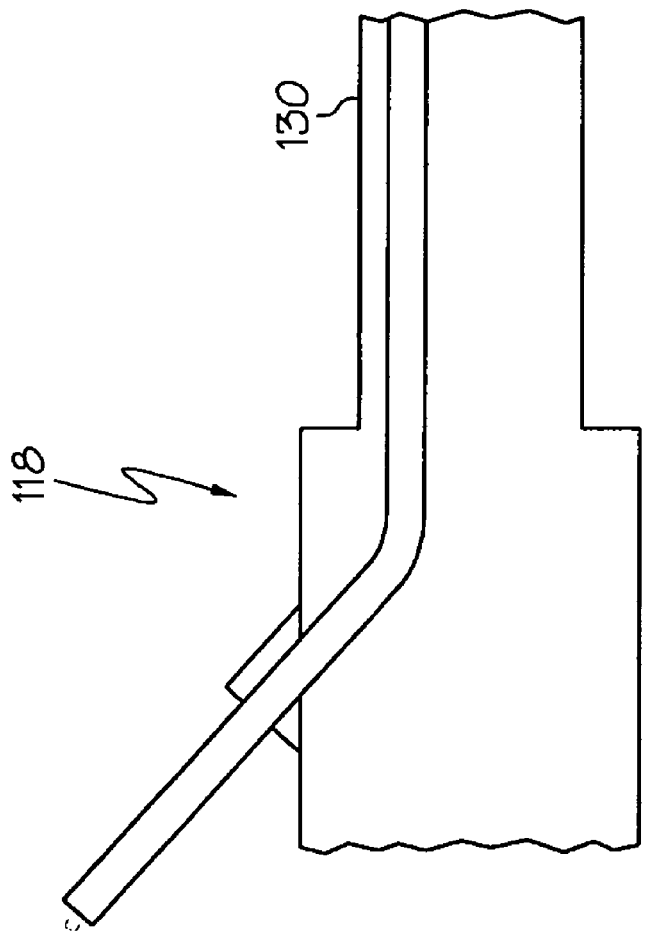

In a second deployment (shown in the alternate embodiment of FIG. 4), a guidewire structure 110 includes the working portion 14 shown in FIG. 1, but the guidewire structure 110 is employed as a non-loop-track in a different medical instrument 118 having a catheter 130. Here, the smallest-diameter end 32 of the working portion 14 is a free end of the medical guidewire 112.

Figure 5:
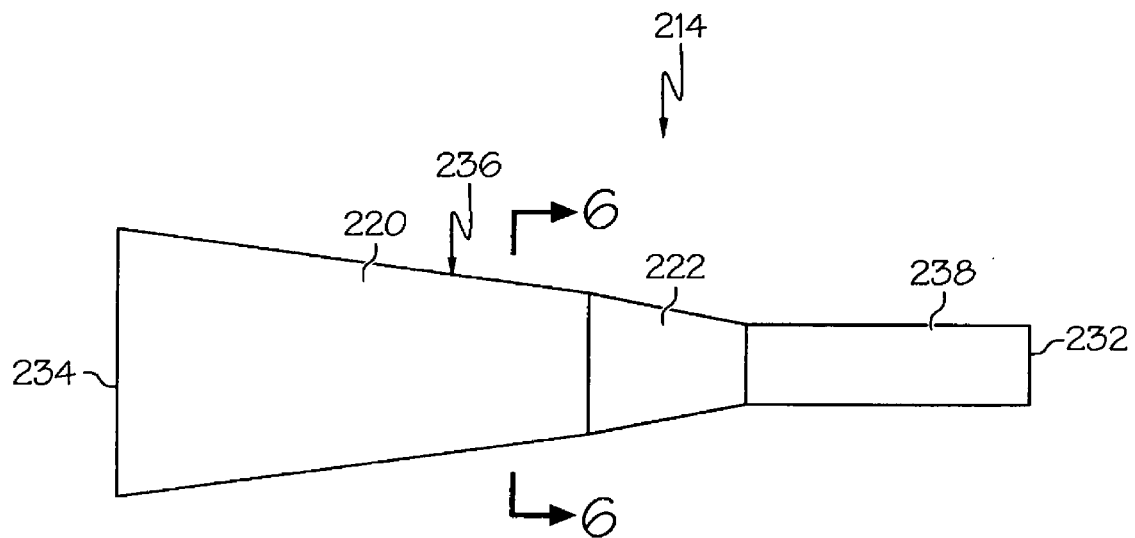
FIG. 5 is a side elevational, shortened view of a working portion of a second embodiment of a guidewire structure of the invention.
Figure 6:
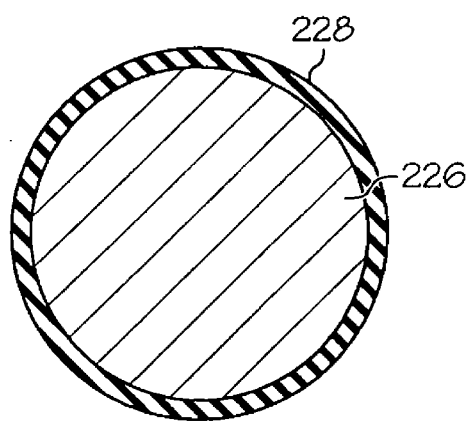
FIG. 6 is a cross-sectional view of the working portion of FIG. 5 taken along lines 6-6 of FIG. 5.
Figure 7:
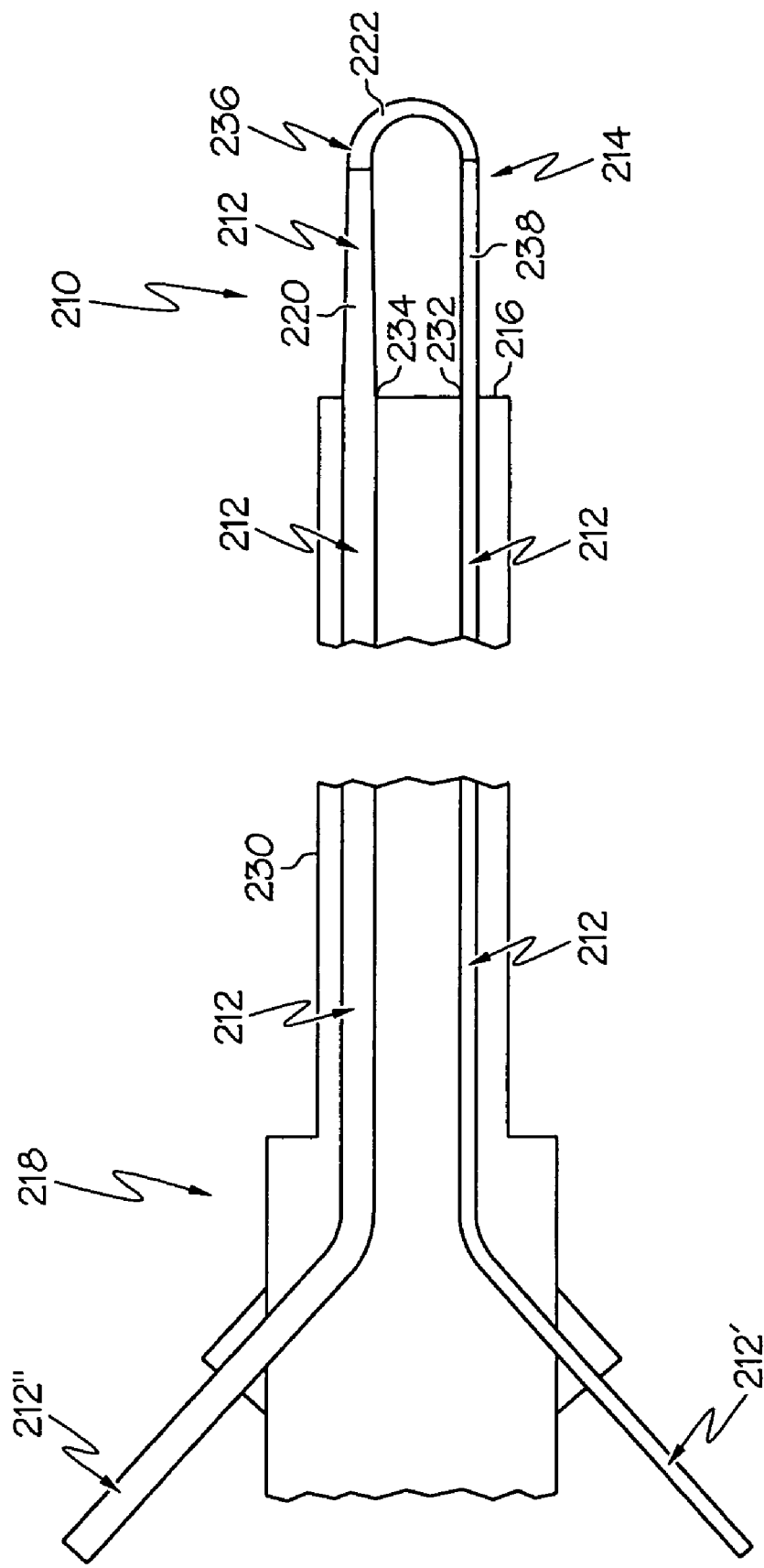
FIG. 7 is a schematic side-elevational cutaway view of a guidewire structure having the working portion shown in FIG. 5 and employed as a loop-track guidewire in an embodiment of a medical instrument having a catheter, wherein the entire working portion is shown extending beyond the distal end of the catheter.

A second embodiment of a guidewire structure 210 of the invention is shown in FIGS. 5-7 and includes a medical guidewire 212 having a working portion 214 which is extendable beyond a distal end 216 of a medical instrument 218. The working portion 214 has a length, and the working portion 214 includes a tapered portion 236 for over fifty percent of the length of the working portion 214.

In one illustration of the embodiment of FIGS. 5-7, the working portion 214 includes a non-tapered portion 238 having a substantially constant cross-section for over twenty-five percent of the length of the working portion 214. In one variation, the non-tapered portion 238 lengthwise adjoins the tapered portion 236. In one modification, the working portion 214 consists essentially of the tapered portion 236 and the non-tapered portion 238. In one example, the cross section of the non-tapered portion 238 is substantially identical to a smallest cross section of the tapered portion 236.

In one enablement of the embodiment of FIGS. 5-7, the tapered portion 236 includes lengthwise adjoining first and second segments 220 and 222, wherein the first segment 220 has a substantially constant first taper, wherein the second segment 222 has a substantially constant second taper, and wherein the first taper is less than the second taper. In one example, the first segment is substantially 4 meters long and tapers from a 0.040-inch cross-sectional diameter to a 0.020-inch cross-sectional diameter, the second segment is substantially 0.5 meters long and tapers from a 0.020-inch cross-sectional diameter to a 0.010-inch cross-sectional diameter, and the non-tapered portion is substantially 2 meters long with a substantially constant 0.010-inch cross-sectional diameter.

In one implementation of the embodiment of FIGS. 5-7, the first segment 220 has a first color and the second segment 222 has a different second color. In one variation, the non-tapered portion 238 has a different third color. In the same or a different implementation, the working portion 214 includes a core wire 226 and includes a lubricious sleeve 228 surrounding, and attached to, the core wire 226. In one variation, the core wire 226 consists essentially of a monolithic length of nitinol.

In a first deployment of the embodiment of FIGS. 5-7, the working portion 214 is extendable as a loop track (as shown in FIG. 7) beyond the distal end 216 of the medical instrument 218. Here, the length of the working portion 214 is a loop-track length of the working portion 214. In one variation, the medical instrument 218 has a catheter 230, and the distal end 216 is the distal end of the catheter 230. In one construction, the loop-track length of the working portion 214 is at least six feet, and the working portion 214 has a substantially circular cross-section having a maximum diameter which is always less than 0.050-inch and a minimum diameter which is always at least 0.010-inch.

In a first arrangement of the embodiment of FIGS. 5-7, the working portion 214 extends as a loop track, and the medical guidewire 212 includes a first leg 212' and a second leg 212". The first leg 212' is monolithically attached to and extends from a first end 232 of the working portion 214 (which is an end of the non-tapered portion 238) proximally through a first passageway of the catheter 230 and outside the medical instrument 218. The second leg 212" is monolithically attached to and extends from a second end 234 of the working portion 214 (which is a largest diameter end of the tapered portion 236) proximally through a second passageway of the catheter 230 and outside the medical instrument 218. In a second arrangement, not shown, the first and second legs 212' and 212" extend through a single passageway such as a working channel of the catheter. In a third arrangement, not shown, the loop track extends beyond the distal end of the catheter from outside the exterior surface of the catheter with the first and/or second legs engaged by guide ways on the exterior surface of the catheter. Other arrangements are left to the artisan.

A second method for using a medical instrument 218 includes steps a) through d). The medical instrument 218 includes a catheter 230 having a distal end and includes a guidewire structure 210. The guidewire structure 210 includes a medical guidewire 212 operatively connected to the catheter 230. The medical guidewire 212 includes a working portion 214 which is extendable beyond the distal end of the catheter 230, wherein the working portion 214 has a length, and wherein the working portion 214 consists essentially of a tapered portion 236 for over fifty percent of the length of the working portion 214 and a non-tapered portion 238 having a substantially constant diameter and extending for over twenty-five percent of the length of the working portion 214. The medical guidewire 212 includes a first guidewire leg 212' having a free end disposed outside the medical instrument 218 and outside a patient and leading to a smallest-diameter first end 232 of the working portion 214 and includes a second guidewire leg 212" having a free end disposed outside the medical instrument 218 and outside the patient and leading to a largest-diameter second end 234 of the working portion 214. Step a) includes inserting the distal end of the catheter 230 an initial distance into a body lumen of the patient. Step b) includes pushing the first guidewire leg 212' to extend at least some of a smaller-diameter region of the working portion 214 beyond the distal end of the catheter 230. Step c) includes pushing the second guidewire leg 212" to extend at least some of a larger-diameter tapered region of the working portion 214 beyond the distal end of the catheter 230 and to temporarily anchor the larger-diameter tapered region of the working portion 214 against a wall of the body lumen. Step d) includes immobilizing the second guidewire leg 212" with respect to the catheter 230 and pushing the catheter 230 a further distance into the body lumen while pulling on the first guidewire leg 212' to retract at least some of the larger-diameter tapered region of the working portion 214.

Figure 8:
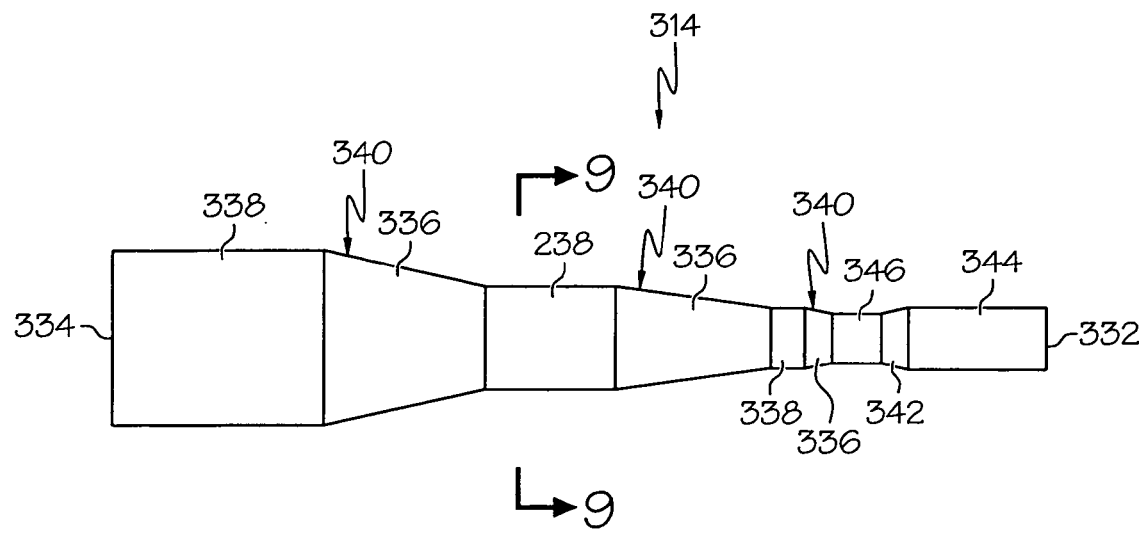
FIG. 8 is a side elevational, shortened view of a working portion of a third embodiment of a guidewire structure of the invention.
Figure 9:
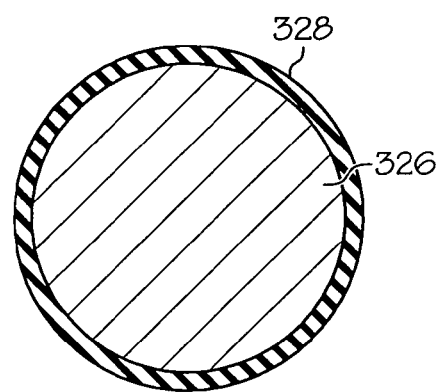
FIG. 9 is a cross-sectional view of the working portion of FIG. 8 taken along lines 9-9 of FIG. 8.
Figure 10:
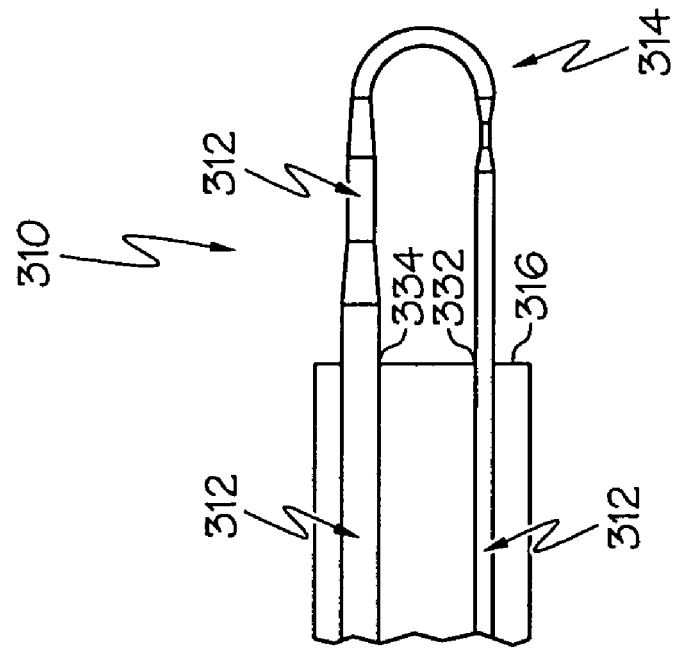
FIG. 10 is a schematic side-elevational cutaway view of a guidewire structure having the working portion shown in FIG. 8 and employed as a loop-track guidewire in an embodiment of a medical instrument having a catheter, wherein the entire working portion is shown extending beyond the distal end of the catheter.
Figure 10:
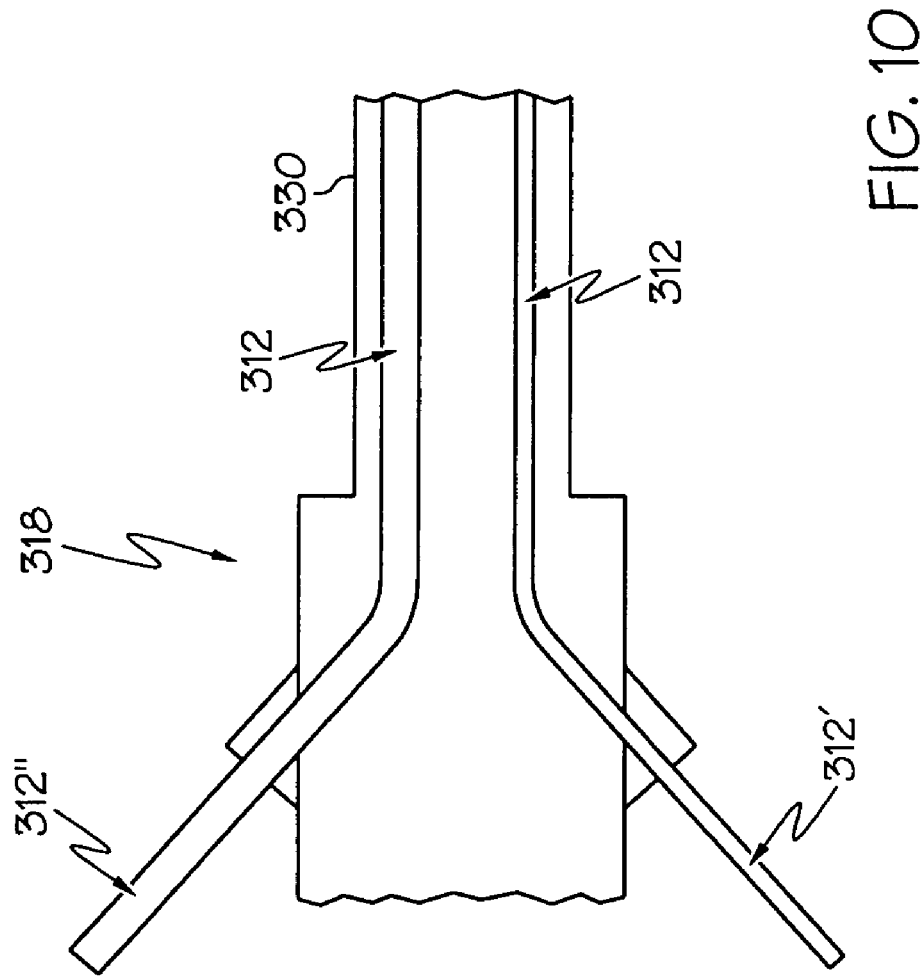

A third embodiment of a guidewire structure 310 of the invention is shown in FIGS. 8-10 and includes a medical guidewire 312 having a working portion 314 which is extendable beyond a distal end 316 of a medical instrument 318. The working portion 314 has a length, and the working portion 314 includes a plurality of lengthwise-adjoining segment pairs 340 for over fifty percent of the length of the working portion 314. Each segment pair 340 consists essentially of a non-tapered segment 338 having a substantially constant cross section and a tapered segment 336 lengthwise adjoining the non-tapered segment 338.

In one illustration of the embodiment of FIGS. 8-10, the working portion 314 includes a diverging segment 342, a substantially constant cross section segment 344 lengthwise-adjoining the diverging segment 342, and a joining segment 346 lengthwise adjoining the diverging segment 342 and lengthwise adjoining one of the tapered segments 336 having a smallest cross section. In one variation, the cross section of the joining segment 346 is substantially constant and identical to the smallest cross section of the one tapered segment 336. In one modification, the lengthwise adjoining segment pairs 340 have a total length of over fifty percent of the length of the working portion 314, the diverging segment 342 and the substantially constant cross section segment 344 have a total length of over twenty-five percent of the length of the working portion 314, and the joining segment 346 has a length of less than one percent of the length of the working portion 314. In one utilization, the joining segment 346 acts as a hinge.

In one example of the embodiment of FIGS. 8-10, there are three segment pairs 340 wherein a first one of the non-tapered segments 338 (the leftmost one in FIG. 8) is substantially 150 centimeters long with a substantially constant 0.045-inch cross-sectional diameter, and a first one of the tapered segments 336 (the leftmost one in FIG. 8) is substantially 25 centimeters long and tapers from a 0.045-inch cross-sectional diameter to a 0.030-inch cross-sectional area. In this example, a second one of the non-tapered segments 338 (the middle one in FIG. 8) is substantially 150 centimeters long with a substantially constant 0.030-inch cross-sectional diameter, and a second one of the tapered segments 336 (the middle one in FIG. 8) is substantially 25 centimeters long and tapers from a 0.030-inch cross-sectional diameter to a 0.018-inch cross-sectional diameter. In this example, a third one of the non-tapered segments 338 (the rightmost one in FIG. 8) is substantially 5 centimeters long with a substantially constant 0.018-inch cross-sectional diameter, and a third one of the tapered segments 336 (the rightmost one in FIG. 8) is substantially 4.75 centimeters long and tapers from a 0.018-inch cross-sectional diameter to a 0.010-inch cross-sectional diameter. In this example, the joining segment 346 is substantially 0.5 centimeters long with a substantially constant 0.010-inch cross-sectional diameter. In this example, the diverging segment 342 is substantially 4.75 centimeters long and diverges from a substantially 0.010-inch cross-sectional area to a 0.018-inch cross-sectional area. In this example, the substantially constant cross section segment 344 is substantially 175 centimeters long and has a substantially constant 0.018-inch cross-sectional diameter.

In one implementation of the embodiment of FIGS. 8-10, the working portion 314 includes a core wire 326 and includes a lubricious sleeve 328 surrounding, and attached to, the core wire 326. In one variation, the core wire 326 consists essentially of a monolithic length of nitinol.

In a first deployment of the embodiment of FIGS. 8-10, the working portion 314 is extendable as a loop track (as shown in FIG. 10) beyond the distal end 316 of the medical instrument 318. Here, the length of the working portion 314 is a loop-track length of the working portion 314. In one variation, the medical instrument 318 has a catheter 330, and the distal end 316 is the distal end of the catheter 330. In one construction, the loop-track length of the working portion 314 is at least six feet, and the working portion 314 has a substantially circular cross-section having a maximum diameter which is always less than 0.050-inch and a minimum diameter which is always at least 0.010-inch.

In a first arrangement of the embodiment of FIGS. 8-10, the working portion 314 extends as a loop track, and the medical guidewire 312 includes a first leg 312' and a second leg 312". The first leg 312' is monolithically attached to and extends from a first end 332 of the working portion 314 (which is an end of the substantially constant cross section segment 344) proximally through a first passageway of the catheter 330 and outside the medical instrument 318. The second leg 312" is monolithically attached to and extends from a second end 334 of the working portion 314 (which is a largest-diameter end of the plurality of segment pairs 340) proximally through a second passageway of the catheter 330 and outside the medical instrument 318. In a second arrangement, not shown, the first and second legs 312' and 312" extend through a single passageway such as a working channel of the catheter. In a third arrangement, not shown, the loop track extends beyond the distal end of the catheter from outside the exterior surface of the catheter with the first and/or second legs engaged by guide ways on the exterior surface of the catheter. Other arrangements are left to the artisan.

A third method for using a medical instrument 318 includes steps a) through d). The medical instrument 318 includes a catheter 330 having a distal end and includes a guidewire structure 310. The guidewire structure 310 includes a medical guidewire 312 operatively connected to the catheter 330. The medical guidewire 312 includes a working portion 314 which is extendable beyond the distal end of the catheter 330, wherein the working portion 314 has a length, and wherein the working portion 314 consists essentially of a plurality of segment pairs 340 for over fifty percent of the length of the working portion 314 lengthwise adjoining a joining segment 346 lengthwise adjoining a diverging segment 342 lengthwise adjoining a substantially constant cross section segment 344. Each segment pair 340 consists essentially of a non-tapered segment 338 having a substantially constant diameter and a tapered segment 336. The medical guidewire 212 includes a first guidewire leg 312' having a free end disposed outside the medical instrument 318 and outside a patient and leading to a first end 332 of the working portion 314 which is an end of the substantially constant cross section segment 344 and includes a second guidewire leg 312" having a free end disposed outside the medical instrument 318 and outside the patient and leading to a second end 334 of the working portion 314 which is a largest-diameter end of the plurality of segment pairs 340. Step a) includes inserting the distal end of the catheter 330 an initial distance into a body lumen of the patient. Step b) includes pushing the first guidewire leg 312' to extend at least some of the substantially constant cross section segment 344 beyond the distal end of the catheter 330. Step c) includes pushing the second guidewire leg 312" to extend at least some of the plurality of segment pairs 340 beyond the distal end of the catheter 330 and to temporarily anchor the extended segment pairs 340 against a wall of the body lumen. Step d) includes immobilizing the second guidewire leg 312" with respect to the catheter 330 and pushing the catheter 330 a further distance into the body lumen while pulling on the first guidewire leg 312' to retract at least some of the extended segment pairs 340.

Several benefits and advantages are obtained from one or more of the embodiments of the invention. In one application, having a loop-track or non-loop-track medical guidewire with a tapered portion for over fifty percent, or for substantially one-hundred percent, of the length of the working portion of the medical guidewire will allow a smaller-cross-sectioned leading portion of the guidewire to be extended into a body lumen of a patient which should result in less insertion force and will allow a larger-cross-sectioned trailing portion extending into the body lumen to handle the mass of an endoscope insertion tube which is to be advanced along the extended larger-cross-sectioned trailing portion of the guidewire. The same reasoning applies to a loop-track or non-loop-track medical guidewire with a plurality of lengthwise spaced apart tapered segments having an intervening non-tapered segment of substantially constant cross section.

While the present invention has been illustrated by a description of several embodiments, methods, and examples, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A guidewire structure comprising a medical guidewire including a working portion which is the maximum portion of the medical guidewire which can be extendable beyond the distal end of the medical instrument, and which is retractable within and extendable beyond a distal end of a medical instrument, wherein the working portion has a length, and wherein the working portion is tapered from a proximal end having a first cross-sectional diameter to a distal end having a second, smaller cross-sectional diameter for substantially one-hundred percent of the length of the working portion, wherein the working portion is extendable as a loop-track beyond the distal end of the medical instrument, and wherein the length of the working portion is a loop-track length of the working portion.

2. The guidewire structure of claim 1, wherein the working portion includes lengthwise adjoining first and second segments, the second segment being disposed distally from the first segment, wherein the first segment has a substantially constant first taper, wherein the second segment has a substantially constant second taper, and wherein the first taper is greater than the second taper.

3. The guidewire structure of claim 2, wherein the first segment has a first color and the second segment has a different second color.

4. The guidewire structure of claim 1, wherein the loop-track length of the working portion is at least six feet and wherein the working portion has a substantially circular cross-section having a maximum diameter which is always less than 0.050-inch and a minimum diameter which is always at least 0.010-inch.

5. A guidewire structure comprising a medical guidewire including a working portion which is the maximum portion of the medical guidewire which can be extendable beyond the distal end of the medical instrument, and which is retractable within and extendable beyond a distal end of a medical instrument, wherein the working portion has a length, and wherein the working portion includes a tapered portion, tapering from a proximal end having a first cross-sectional diameter to a distal end having a second, smaller cross-sectional diameter, which extends for over fifty percent of the length of the working portion wherein the working portion is extendable as a loop-track beyond the distal end of the medical instrument, and wherein the length of the working portion is a loop-track length of the working portion.

6. The guidewire structure of claim 5, wherein the working portion includes a non-tapered portion having a substantially constant cross-section, oriented transversally to the length of the working portion, for over twenty-five percent of the length of the working portion, wherein the non-tapered portion lengthwise adjoins the distal end of the tapered portion, wherein the working portion consists essentially of the tapered portion and the non-tapered portion, and wherein the cross section of the non-tapered portion is substantially identical to a smallest cross section of the tapered portion.

7. The guidewire structure of claim 6, wherein the tapered portion includes lengthwise adjoining first and second segments, the second segment being disposed distally from the first segment, wherein the first segment has a substantially constant first taper, wherein the second segment has a substantially constant second taper, and wherein the first taper is less than the second taper.

8. The guidewire structure of claim 7, wherein the first segment has a first color, the second segment has a different second color, and the non-tapered portion has a different third color.

9. The guidewire structure of claim 5, wherein the working portion includes a core wire and includes a lubricious sleeve surrounding, and attached to, the core wire.

10. The guidewire structure of claim 9, wherein the core wire consists essentially of a monolithic length of nitinol.

11. The guidewire structure of claim 5, wherein the loop-track length of the working portion is at least six feet and wherein the working portion has a substantially circular cross-section having a maximum diameter which is always less than 0.050-inch and a minimum diameter which is always at least 0.010-inch.

12. A method for using a medical instrument, wherein the medical instrument includes a catheter having a distal end and includes a guidewire structure, wherein the guidewire structure includes a medical guidewire operatively connected to the catheter, wherein the medical guidewire includes a working portion which is the maximum portion of the medical guidewire which can be extendable beyond the distal end of the medical instrument, and which is retractable within and extendable beyond the distal end of the catheter, wherein the working portion has a length, wherein the working portion is extendable as a loop-track beyond the distal end of the medical instrument, and wherein the length of the working portion is a loop-track length of the working portion, wherein the working portion is tapered from a proximal end having a first cross-sectional diameter to a distal end having a second, smaller cross-sectional diameter for substantially one-hundred percent of the length of the working portion, wherein the medical guidewire includes a first guidewire leg having a free end disposed outside the medical instrument and outside a patient and leading to a smallest-diameter first end of the working portion and includes a second guidewire leg having a free end disposed outside the medical instrument and outside the patient and leading to a largest-diameter second end of the working portion, and wherein the method comprises the steps of:
  a) inserting the distal end of the catheter an initial distance into a body lumen of the patient;
  b) pushing the first guidewire leg to extend at least some of a smaller-diameter tapered region of the working portion beyond the distal end of the catheter;
  c) pushing the second guidewire leg to extend at least some of a larger-diameter tapered region of the working portion beyond the distal end of the catheter and to temporarily anchor the larger-diameter tapered region of the working portion against a wall of the body lumen; and
  d) immobilizing the second guidewire leg with respect to the catheter and pushing the catheter a further distance into the body lumen while pulling on the first guidewire leg to retract at least some of the larger-diameter tapered region of the working portion.

13. A method for using a medical instrument, wherein the medical instrument includes a catheter having a distal end and includes a guidewire structure, wherein the guidewire structure includes a medical guidewire operatively connected to the catheter, wherein the medical guidewire includes a working portion which is the maximum portion of the medical guidewire which can be extendable beyond the distal end of the medical instrument, and which is retractable within and extendable beyond the distal end of the catheter, wherein the working portion has a length, wherein the working portion is extendable as a loop-track beyond the distal end of the medical instrument, and wherein the length of the working portion is a loop-track length of the working portion, wherein the working portion consists essentially of a tapered portion, tapering from a proximal end having a first cross-sectional diameter to a distal end having a second, smaller cross-sectional diameter, which extends for over fifty percent of the length of the working portion and a non-tapered portion having a substantially constant diameter and extending for over twenty-five percent of the length of the working portion, wherein the medical guidewire includes a first guidewire leg having a free end disposed outside the medical instrument and outside a patient and leading to a smallest-diameter first end of the working portion and includes a second guidewire leg having a free end disposed outside the medical instrument and outside the patient and leading to a largest-diameter second end of the working portion, and wherein the method comprises the steps of:
  a) inserting the distal end of the catheter an initial distance into a body lumen of the patient;
  b) pushing the first guidewire leg to extend at least some of a smaller-diameter region of the working portion beyond the distal end of the catheter;
  c) pushing the second guidewire leg to extend at least some of a larger-diameter tapered region of the working portion beyond the distal end of the catheter and to temporarily anchor the larger-diameter tapered region of the working portion against a wall of the body lumen; and d) immobilizing the second guidewire leg with respect to the catheter and pushing the catheter a further distance into the body lumen while pulling on the first guidewire leg to retract at least some of the larger-diameter tapered region of the working portion.

14. The guidewire structure of claim 1, wherein the working portion includes lengthwise adjoining first and second segments, the second segment being disposed distally from the first segment, wherein the first segment has a substantially constant first taper, wherein the second segment has a substantially constant second taper, and wherein the first taper is less than the second taper.

15. The guidewire structure of claim 6, wherein the tapered portion includes lengthwise adjoining first and second segments, the second segment being disposed distally from the first segment, wherein the first segment has a substantially constant first taper, wherein the second segment has a substantially constant second taper, and wherein the first taper is greater than the second taper.

16. The guidewire structure of claim 1, wherein the guidewire structure includes a first leg configured extend from a portion of the medical instrument which remains outside of a patient to a first end of the working portion, the first end being a smallest-diameter end of the working portion, and a second leg configured to extend from a portion of the medical instrument which remains outside of a patient to a second end of the working portion, the second end being a largest-diameter end of the working portion.

17. The guidewire structure of claim 16, wherein said smallest-diameter end has a substantially circular cross section, and said largest-diameter end has a substantially circular cross section.

18. The guidewire structure of claim 5, wherein the guidewire structure includes a first leg configured extend from a portion of the medical instrument which remains outside of a patient to a first end of the working portion, the first end being a smallest-diameter end of the working portion, and a second leg configured to extend from a portion of the medical instrument which remains outside of a patient to a second end of the working portion, the second end being a largest-diameter end of the working portion.

19. The guidewire structure of claim 18, wherein said smallest-diameter end has a substantially circular cross section, and said largest-diameter end has a substantially circular cross section.

* * * * *